(12) United States Patent
Yoo et al.

(10) Patent No.: US 9,880,077 B2
(45) Date of Patent: Jan. 30, 2018

(54) MULTI SAMPLING PORT MONITORING APPARATUS FOR MEASURING POLLUTION LEVEL AND MONITORING METHOD USING THE SAME

(71) Applicant: WITHTECH INC, Daejeon (KR)

(72) Inventors: Seoung-Kyo Yoo, Daejeon (KR); Eung Sun Lee, Daejeon (KR); Hyun Wook Lee, Daejeon (KR)

(73) Assignee: WITHTECH INC, Daejeon (KR)

( * ) Notice: Subject to any disclaimer, the term of this patent is extended or adjusted under 35 U.S.C. 154(b) by 72 days.

(21) Appl. No.: 15/031,567

(22) PCT Filed: Oct. 23, 2014

(86) PCT No.: PCT/KR2014/010011
§ 371 (c)(1),
(2) Date: Apr. 22, 2016

(87) PCT Pub. No.: WO2015/060664
PCT Pub. Date: Apr. 30, 2015

(65) Prior Publication Data
US 2016/0282235 A1    Sep. 29, 2016

(30) Foreign Application Priority Data
Oct. 23, 2013 (KR) .......................... 10-2013-0126629

(51) Int. Cl.
*G01N 1/26* (2006.01)
*G01N 15/06* (2006.01)
(Continued)

(52) U.S. Cl.
CPC ............... *G01N 1/26* (2013.01); *G01N 15/06* (2013.01); *G01N 33/0011* (2013.01);
(Continued)

(58) Field of Classification Search
CPC .. G01N 15/06; G01N 1/26; G01N 2015/0046; G01N 33/0011; G01N 35/08; G01N 35/1095; G01N 35/1097
See application file for complete search history.

(56) References Cited

U.S. PATENT DOCUMENTS 3,592,605 A * 7/1971 Noma et al. ......... G01N 35/025
29/259
4,856,352 A * 8/1989 Daum .................. G01N 1/2247
73/1.06
(Continued)

FOREIGN PATENT DOCUMENTS

JP    S60120230 A    6/1985
JP    H0560867 A     3/1993
(Continued)

OTHER PUBLICATIONS

Japan Patent Office, Office Action Issued in Application No. 2016-525995, dated May 30, 2017, 7 pages (Submitted with Machine Translation).
(Continued)

*Primary Examiner* — Francis Gray
(74) *Attorney, Agent, or Firm* — McCoy Russell LLP

(57) ABSTRACT

Provided are a multi sampling port monitoring apparatus for measuring a pollution level in a predetermined space and a monitoring method using the same. More particularly, provided are a multi sampling port monitoring apparatus capable of effectively monitoring a pollution level in a wide space by including a plurality of sampling ports so that air is sucked at several points in a space to be measured, measuring an average pollution level of the air sucked from the plurality of sampling ports, and allowing pollution levels of the air sucked from the sampling ports to be individually measured in the case in which the average pollution level is
(Continued)

out of a predetermined range, and a monitoring method using the same.

11 Claims, 6 Drawing Sheets

(51) Int. Cl.
    *G01N 33/00*     (2006.01)
    *G01N 35/08*     (2006.01)
    *G01N 15/00*     (2006.01)
    *G01N 35/10*     (2006.01)

(52) U.S. Cl.
    CPC ......... *G01N 35/08* (2013.01); *G01N 35/1097* (2013.01); *G01N 35/1095* (2013.01); *G01N 2015/0046* (2013.01)

(56) References Cited

U.S. PATENT DOCUMENTS

| | | | |
|---|---|---|---|
| 5,553,496 A * | 9/1996 | Nishiyama | G01N 1/26 454/187 |
| 6,125,710 A * | 10/2000 | Sharp | G01N 1/26 73/863.01 |
| 6,615,679 B1 | 9/2003 | Knollenberg et al. | |
| 2005/0217351 A1 | 10/2005 | Kreck et al. | |
| 2011/0189052 A1* | 8/2011 | Jaeggi | G01N 35/085 422/68.1 |
| 2012/0048000 A1* | 3/2012 | Kirzhner | F02C 7/22 73/40.5 R |
| 2013/0081482 A1 | 4/2013 | Yamasaki | |

FOREIGN PATENT DOCUMENTS

| | | |
|---|---|---|
| JP | 2003344239 A | 12/2003 |
| JP | 2005221242 A | 8/2005 |
| JP | 2005279575 A | 10/2005 |
| KR | 1020060036687 A | 5/2006 |
| KR | 20080105654 A | 12/2008 |
| KR | 20110026918 A | 3/2011 |
| KR | 101213641 B1 | 12/2012 |
| WO | 0163250 A1 | 8/2001 |

OTHER PUBLICATIONS

ISA Korean Intellectual Property Office, International Search Report Issued in Application No. PCT/KR2014/010011, dated Jan. 27, 2015, WIPO, 2 pages.

* cited by examiner

MULTI SAMPLING PORT MONITORING APPARATUS FOR MEASURING POLLUTION LEVEL AND MONITORING METHOD USING THE SAME

CROSS REFERENCE TO RELATED APPLICATIONS

The present application is a U.S. National Phase of International Patent Application Serial No. PCT/KR2014/010011, entitled "MULTI SAMPLING PORT MONITORING APPARATUS FOR MEASURING POLLUTION LEVEL AND MONITORING METHOD USING THE SAME," filed on Oct. 23, 2014, which claims priority to Korean Patent Application No. 10-2013-0126629, entitled "MULTI SAMPLING PORT MONITORING APPARATUS FOR MEASURING POLLUTION LEVEL AND MONITORING METHOD USING THE SAME," filed on Oct. 23, 2013, the entire contents of each of which are hereby incorporated by reference for all purposes.

TECHNICAL FIELD

The present invention relates to a multi sampling port monitoring apparatus for measuring a pollution level in a predetermined space and a monitoring method using the same, and more particularly, to a multi sampling port monitoring apparatus capable of effectively monitoring a pollution level in a wide space by including a plurality of sampling ports so that air is sucked at several points in a space to be measured, measuring an average pollution level of the air sucked from the plurality of sampling ports, and allowing pollution levels of the air sucked from the sampling ports to be individually or partially measured in the case in which the average pollution level is out of a predetermined range, and a monitoring method using the same.

BACKGROUND ART

A clean room, a place in which a semiconductor manufacturing process, or the like, is performed, is divided into several classes depending on cleanliness, which is determined by the number of particles present per unit area and having a predetermined size, and a pollution cause should be frequently recognized through precise measurement in order to always maintain and manage a predetermined level of cleanliness.

Therefore, an important portion that may have an influence on the cleanliness should be recognized and frequently measured, and an accidental situation should be able to be predicted by regularly measuring several places in the clean room. Further, in the clean room, it is important to constantly maintain and manage temperature, humidity, and pressure as well as recognize the cleanliness by analyzing particles.

Generally, in the clean room of a semiconductor manufacturing facility, a particle measuring apparatus is used to test a leak for a filter of the clean room and measure internal particles of the clean room. After the filter provided on a ceiling of the clean room is installed, it is damaged due to internal and external changes, such that a filtering function thereof may be deteriorated.

Therefore, it is required to test the leak for the filter in order to verify stable clean room securing and reliability securing of a semiconductor device. The test of the leak is performed in a scheme of scanning a surface of the filter while maintaining a predetermined distance from a lower end of the filter and measuring the number of particles present in air discharged from the filter.

As a technology relating to this, Korean Patent Laid-Open Publication No. 2006-0036687 (published on May 2, 2006 and entitled 'Particle Probe Apparatus for Clean Room') has been disclosed.

However, since the clean room in which various semiconductor processes are performed has a very wide space, a method of measuring a pollution level by installing a sensor at a specific point is not appropriate for measuring a pollution level in a wide space.

It is difficult for a method of measuring a concentration by installing a sensor at a specific point to represent a concentration in a wide space since it measures only the concentration at the specific point. In the case in which several sensors are installed in order to solve this problem, an economical burden is excessively increased in covering the wide space.

A technology of forming a plurality of sampling ports in one measuring instrument and measuring concentrations in the plurality of sampling ports has been suggested in order to solve this problem. However, since the concentrations in the plurality of sampling ports are sequentially measured by one measuring instrument, there was a disadvantage that it takes a very long time.

RELATED ART DOCUMENT

Patent Document

Korean Patent Laid-Open Publication No. 2006-0036687 (published on May 2, 2006 and entitled 'Particle Probe Apparatus for Clean Room')

DISCLOSURE

Technical Problem

An object of the present invention is to provide a multi sampling port monitoring apparatus capable of effectively monitoring a pollution level in a wide space by including a plurality of sampling ports so that air is sucked at several points in a space to be measured, measuring an average pollution level of the air sucked from the plurality of sampling ports, and allowing pollution levels of the air sucked from the sampling ports to be individually measured in the case in which the average pollution level is out of a predetermined range, and a monitoring method using the same.

Technical Solution

In one general aspect, a multi sampling port monitoring apparatus for measuring a pollution level in a space to be measured includes: a plurality of sampling ports 100 provided so that air is sucked at several points in the space to be measured; suction pipes 200 connected to each sampling port 100; branch pipes 300 branched from the suction pipes 200; a mixing part 500 connected to end portions of the suction pipes 200 and the branch pipes 300 to collect and mix the sucked air; a detecting part 600 measuring a pollution level of the air passing through the mixing part 500 and then introduced thereinto; first control valves 410 connected to the suction pipes 200; second control valves 420 connected to the branch pipes; and a controlling part controlling the first control valves 410, the second control valves 420, and the detecting part 600, wherein the controlling part performs a control to open the first control valves 410, thereby allowing an average pollution level of the air sucked from the plurality of sampling ports 100 to be measured or to close the first control valves 410 and open at least one of the plurality of second control valves 420 so that the air flows toward the branch pipes 300, thereby allowing pollution levels of the air sucked from the sampling ports 100 to be measured.

In the case in which the average pollution level of the air sucked from the plurality of sampling ports 100 is out of a predetermined range, the first control valves 410 may be closed and the plurality of second control valves 420 may be sequentially opened one by one or some of the plurality of second control valves 420 are opened to allow pollution levels of the air sucked from the sampling ports 100 to be measured.

The plurality of sampling ports 100 may be mounted in one separated space or be each mounted in a plurality of separated spaces.

The first control valve 410 may be a solenoid valve provided at a front end of the mixing part 500 to collectively control the plurality of suction pipes 200.

The second control valve 420 may be a 3-way valve provided at a point of the suction pipe 200 from which the branch pipe 300 is branched.

The multi sampling port monitoring apparatus may further include a second flow rate adjusting part 820 disposed between the mixing part 500 and a vacuum pump 830.

The mixing part 500 may have a pipe shape in which pipes each connected to end portions of the plurality of suction pipes 200 and branch pipes 300 are merged as one pipe or have a mixing chamber form including a separate mixing means.

In another general aspect, a multi sampling port monitoring method using the multi sampling port monitoring apparatus 1 as described above includes: a) opening all of the first control valves 410 provided on the plurality of suction pipes 200 and closing all of the second control valves 420; b) measuring, by the detecting part 600, an average pollution level of the air introduced through the suction pipes 200; c) closing all of the first control valves 410 in the case in which the measured average pollution level is out of a preset range; and d) sequentially opening the second control valves 420 one by one to allow pollution levels of the air sucked from each sampling port 100 to be individually measured.

In still another general aspect, a multi sampling port monitoring method using the multi sampling port monitoring apparatus 1 as described above includes: a) opening all of the first control valves 410 provided on the plurality of suction pipes 200 and closing all of the second control valves 420; b) measuring, by the detecting part 600, an average pollution level of the air introduced through the suction pipes 200; c) closing all of the first control valves 410 in the case in which the measured average pollution level is out of a preset range; d) opening a plurality of second control valves 420 depending on a predetermined sequence to allow pollution levels of the air sucked from the sampling ports 100 to be measured; and e) closing some of the opened second control valves 420 to allow pollution levels of the air sucked from the sampling ports 100 to be measured, in the case in which the measured average pollution level is out of the preset range, and closing the opened second control valves 420 and opening the closed second control valves 420 to allow pollution levels of the air sucked from the sampling ports 100 to be measured, in the case in which the measured average pollution level is within the preset range.

Advantageous Effects

The multi sampling port monitoring apparatus and the monitoring method using the same according to the present invention include the plurality of sampling ports so that the air is sucked at several points in the space to be measured, measure the average pollution level of the air sucked from the plurality of sampling ports, and allow pollution levels of the air sucked from the sampling ports to be individually measured in the case in which the average pollution level is out of the predetermined range, thereby making it possible to effectively monitor the pollution level in a wide space.

In addition, in the present invention, several sampling ports are disposed in a wide space, and the average pollution level in the space to be measured is managed, thereby making it possible to rapidly find the pollution source at the time of occurrence of the event.

That is, in the present invention, average data on the pollution levels in a zone in which the sampling ports are mounted is managed, thereby making it possible to manage the pollution level in the wide space using one apparatus, and concentrations in each sampling port are sequentially scanned or are individually scanned by a specific sequence in order to recognize the pollution source when the average pollution level rises, thereby making it possible to rapidly find a pollution zone.

Therefore, in present invention, rapid space pollution level mapping and event capture are possible, one measuring instrument (detecting part) is used, thereby making it possible to remove an error between measuring instruments, and a cost may be significantly decreased as compared with an existing scheme of using several measuring instruments.

DESCRIPTION OF DRAWINGS

The above and other objects, features and advantages of the present invention will become apparent from the following description of preferred embodiments given in conjunction with the accompanying drawings, in which.

BEST MODE

Hereinafter, a multi sampling port monitoring apparatus for measuring a pollution level and a monitoring method using the same according to the present invention will be described in detail with reference to the accompanying drawings.

First, a multi sampling port monitoring apparatus 1 according to the present invention, which is to measure a pollution level in a space to be measured, has been devised particularly so as to effectively measure a pollution level even in a wide space.

Figure 1:
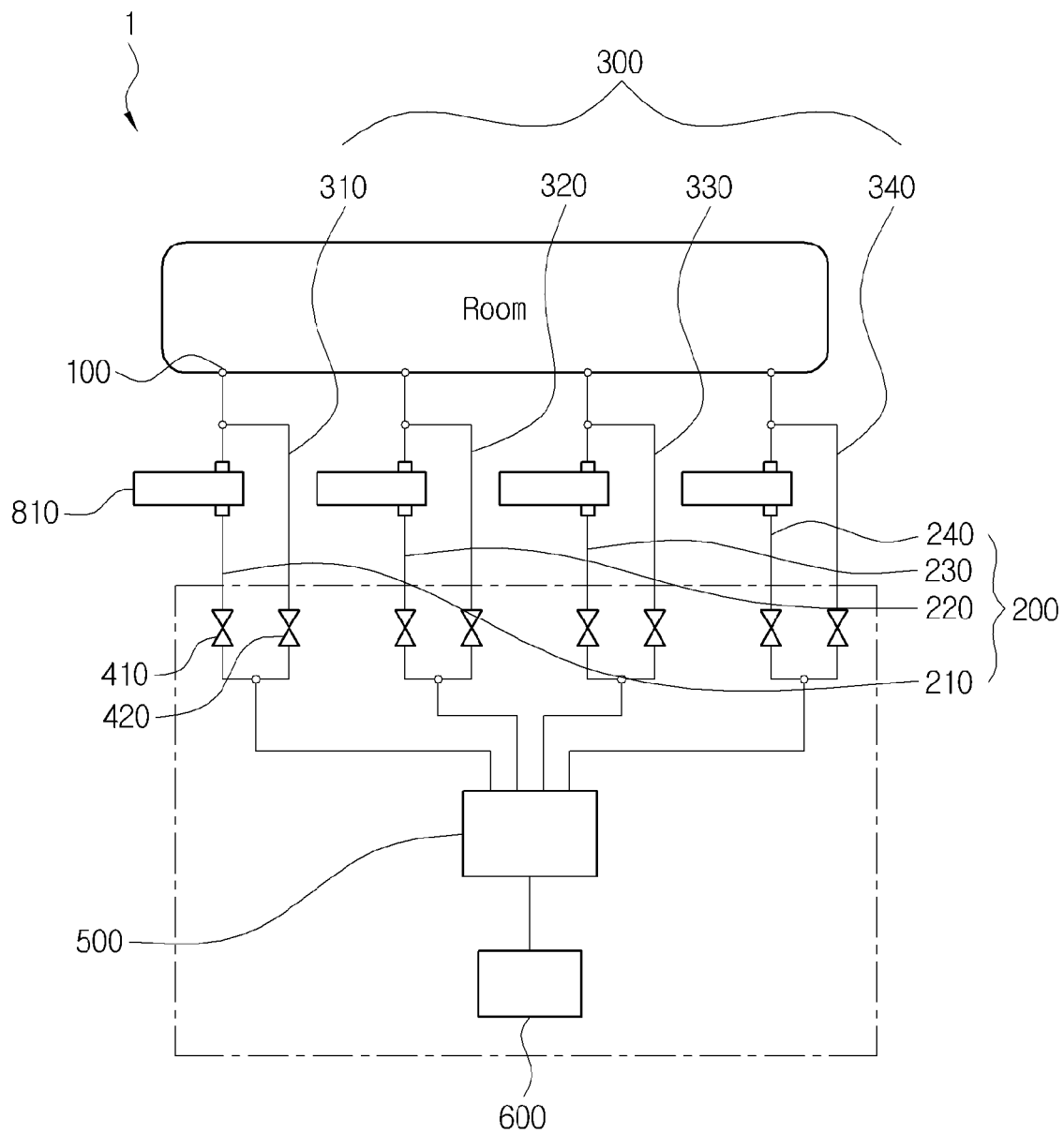
FIGS. 1 to 4 are conceptual diagrams showing various examples of a multi sampling port monitoring apparatus according to the present invention.

As shown in FIG. 1, the multi sampling port monitoring apparatus 1 according to the present invention is configured to include sampling ports 100, suction pipes 200, branch pipes 300, a mixing part 500, a detecting part 600, and a controlling part (not shown).

A plurality of sampling ports 100, which suck air at several points in a space to be measured, are provided.

Here, in the multi sampling port monitoring apparatus 1 according to the present invention, the plurality of sampling ports 100 may be installed in one separated space or may be each installed in a plurality of separated spaces.

Describing a semiconductor clean room by way of example, in the multi sampling port monitoring apparatus 1 according to the present invention, the plurality of sampling ports 100 may be installed at several points in order to recognize which point in one clean room is exposed to pollution.

In addition, when the multi sampling port monitoring apparatus 1 according to the present invention is to measure pollution levels of several semiconductor clean rooms using one equipment, the sampling port 100 may also be installed in each clean room.

The suction pipes 200 are pipes connected to the sampling ports 100, and an air flow may be adjusted by first control valves 410 installed on the suction pipes 200.

The number of suction pipes 200 corresponds to that of sampling ports 100, and the number of first control valves 410 also corresponds to that of sampling ports 100.

Figure 2:
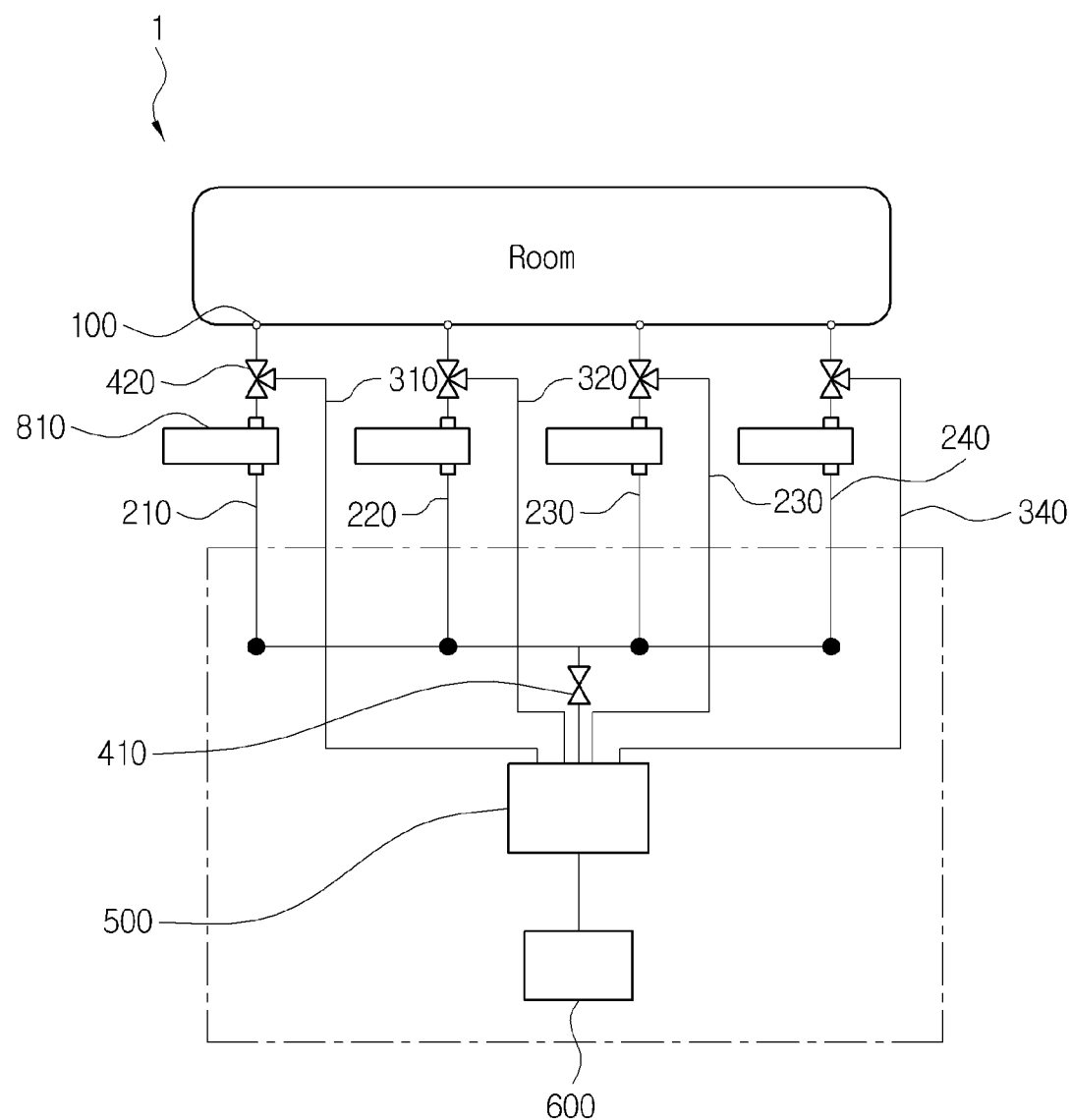

As another example, as shown in FIG. 2, the first control valve 410 is a solenoid valve singly provided at a front end of the mixing part 500 to collectively control the plurality of suction pipes 200.

The branch pipes 300 are pipes branched from the suction pipes 200, and an air flow may be adjusted by second control valves 420 installed on the branch pipes 300.

The suction pipe 200 and the branch pipe 300 are two passages through which air sucked through one sampling port 100 flows, and it is determined depending on opening and closing operations of the first and second control valves 410 and 420 whether or not the air flows.

Here, it is preferable that the first and second control valves 410 and 420 are solenoid valves so that they are easily controlled.

In addition, the second control valve 420 may be a 3-way valve provided at a point of the suction pipe 200 from which the branch pipe 300 is branched as shown in FIG. 2 or be a 2-way valve as shown in FIG. 1.

The mixing part 500, which is connected to end portions of the suction pipes 200 and the branch pipes 300 to collect and mix the air sucked from the plurality of sampling ports 100, may have a pipe shape in which pipes each connected to end portions of the plurality of suction pipes 200 and branch pipes 300 are merged as one pipe.

As another example, the mixing part 500 may be a mixing chamber including a separate mixing means such as an agitator. In addition, the mixing part 500 may be variously modified as long as it may uniformly mix the air sucked from the plurality of suction pipes 200 and branch pipes 300.

The detecting part 600, which is a means measuring a pollution level of the air passing through the mixing part 500 and then introduced thereinto, may include a pump disposed therein in order to suck the air or may include a separate pump attached thereto in the case in which the pump is not disposed therein.

Here, as the detecting part 600, an appropriate kind of equipment may be used depending on a pollution source to be measured or a measuring method.

The controlling part controls operations of the first control valves 410, the second control valves 420, and the detecting part 600.

Particularly, in the present invention, the controlling part simultaneously opens the plurality of first control valves 410 to allow the detecting part 600 to measure an average pollution level of the air sucked from the plurality of sampling ports 100.

In the case in which the average pollution level of the air sucked from the plurality of sampling ports 100 is out of a predetermined range, the controlling part closes the first control valves 410 and sequentially opens the plurality of second control valves 420 one by one or opens some of the plurality of second control vales 420 to allow pollution levels of the air sucked from the sampling ports 100 to be measured.

As shown in FIG. 1, the multi sampling port monitoring apparatus 1 according to the present invention may include first flow rate adjusting parts 810 provided on the suction pipes 200 and adjusting a flow rate of the sucked air.

As described above, the multi sampling port monitoring apparatus 1 according to the present invention sucks the air by opening all of the plurality of suction pipes 200 in order to measure the average pollution level. In this case, an amount of air sucked through each suction pipe 200 is decreased as compared with in the case of sucking the air by opening only one branch pipe 300.

For example, in the case in which four sampling ports 100 are provided, when air of 2.5 lpm is sucked through each suction pipe 200, air of 10 lpm is sucked through one branch pipe 300.

That is, in the multi sampling port monitoring apparatus 1 according to the present invention, since an amount of sample that may be sucked and measured in the detecting part 600 should be constantly maintained, an adjustment should be made so that 1/N (here, N indicates the number of sampling ports 100) of an entire amount of air that may be sucked is introduced through one suction pipe 200.

Therefore, when the multi sampling port monitoring apparatus 1 according to the present invention measures the average pollution level, the air may be sucked at each point through the first flow rate adjusting parts 810 by flow rates set in the suction pipes 200.

In addition, the multi sampling port monitoring apparatus 1 according to the present invention may include a vacuum pump 830 connected to the mixing part 500 and applying negative pressure so that the air from the sampling ports 100 is sucked.

The vacuum pump 830 serves to rapidly suck the air of each sampling port 100 for a rapid reaction in the case in which a suction flow velocity of the detecting part 600 is slow. It is preferable that the multi sampling port monitoring apparatus 1 according to the present invention includes the vacuum pump 830 for rapid suction and analysis of the air since a flow rate of the air sucked through the sampling ports 100 is very small, such that a flow velocity of the air may be very slow.

Figure 3:
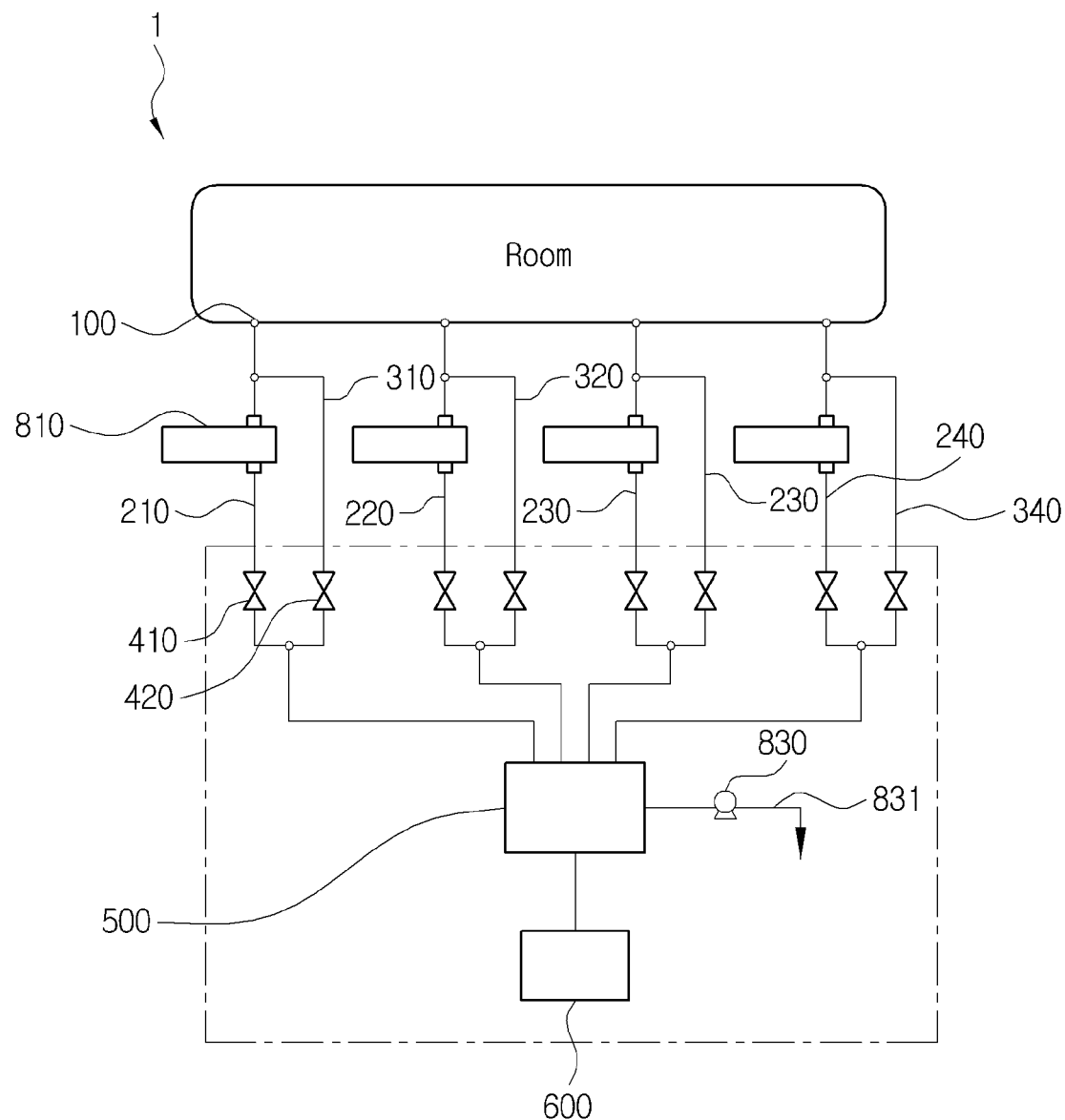

Here, the multi sampling port monitoring apparatus 1 according to the present invention may further include a discharge pipe 831 connected to a rear end of the vacuum pump 830 as shown in FIG. 3 and further include a second flow rate adjusting part 820 disposed between the mixing part 500 and the vacuum pump 830.

Therefore, the multi sampling port monitoring apparatus 1 according to the present invention may uniformly sample a wide space by reflecting an accurate concentration.

As described above, since a flow rate of the air sucked through the sampling ports 100 is a small amount in lpm unit, the multi sampling port monitoring apparatus 1 according to the present invention may allow sampling air except for an amount of air that should be sucked into the detecting part 600 to be discharged through the discharge pipe 831 instead of increasing the flow rate of the air sucked through the sampling ports 100 to increase a flow velocity of the air arriving at the mixing part 500.

That is, the multi sampling port monitoring apparatus 1 according to the present invention sucks a high flow rate by the vacuum pump 830, thereby making it possible to suppress adsorption of the air in the suction pipes 200 and the branch pipes 300 and allow the pollution level to be rapidly and accurately measured by the detecting part 600.

A first example of a monitoring method using the multi sampling port monitoring apparatus 1 having the above-mentioned configuration and feature may include a) opening all of the first control valves 410 provided on the plurality of suction pipes 200 and closing all of the second control valves 420; b) measuring, by the detecting part 600, an average pollution level of the air introduced through the suction pipes 200; c) closing all of the first control valves 410 in the case in which the measured average pollution level is out of a preset range; and d) sequentially opening the second control valves 420 one by one to allow pollution levels of the air sucked from each sampling port 100 to be individually measured.

That is, in the monitoring method according to the present invention, in the case in which a specific event does not occur, all of the first control valves 410 are opened to suck the air through the plurality of sampling ports 100, whereby the average pollution level is measured by the detecting part 600.

In addition, in the case in which the specific event (pollution) occurs, all of the first control valves 410 are closed and the second control valves 420 are sequentially opened one by one, such that the pollution levels of the air sucked through each sampling port 100 are individually measured by the detecting part 600.

Figure 4:
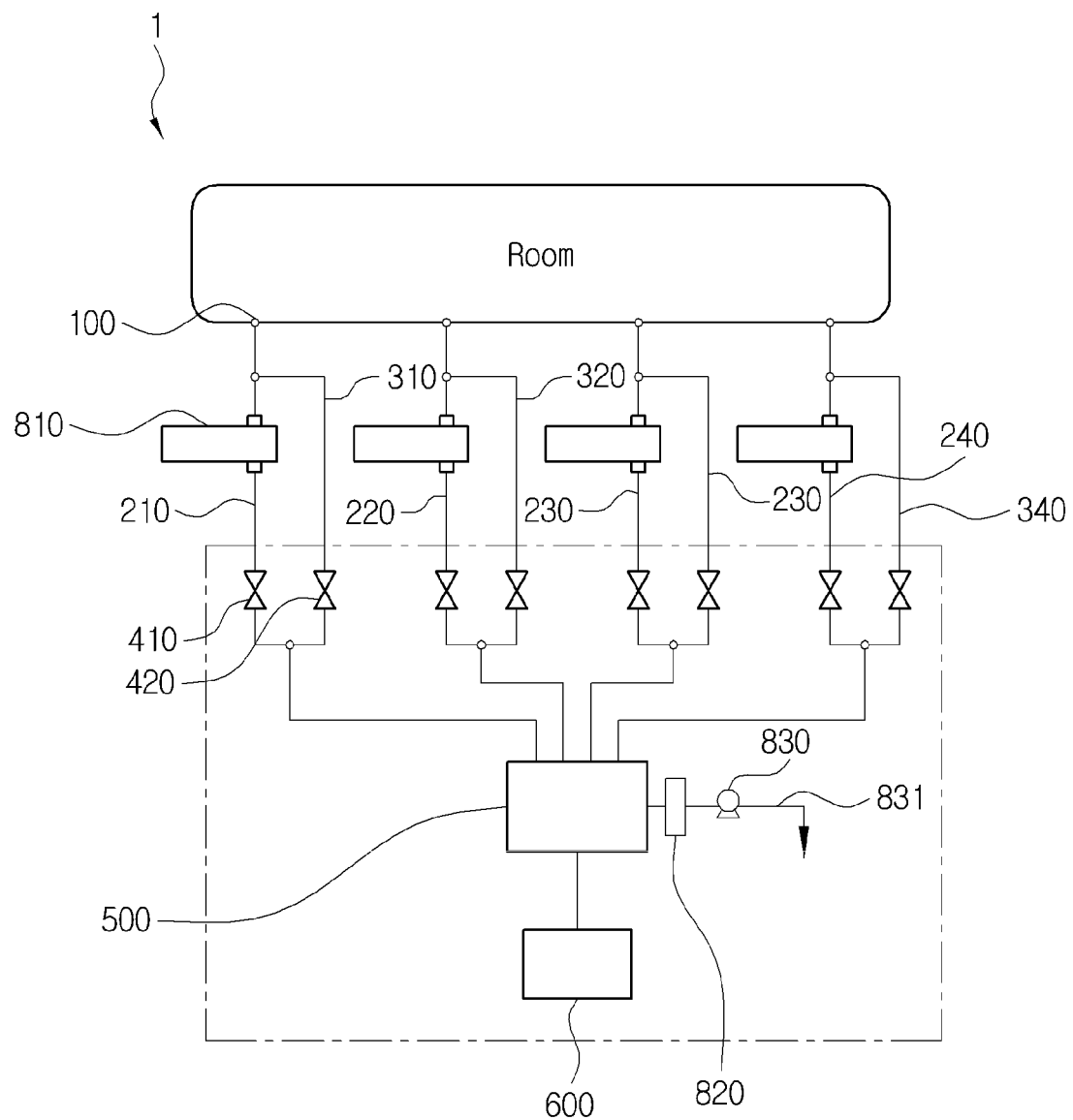
Figure 5:
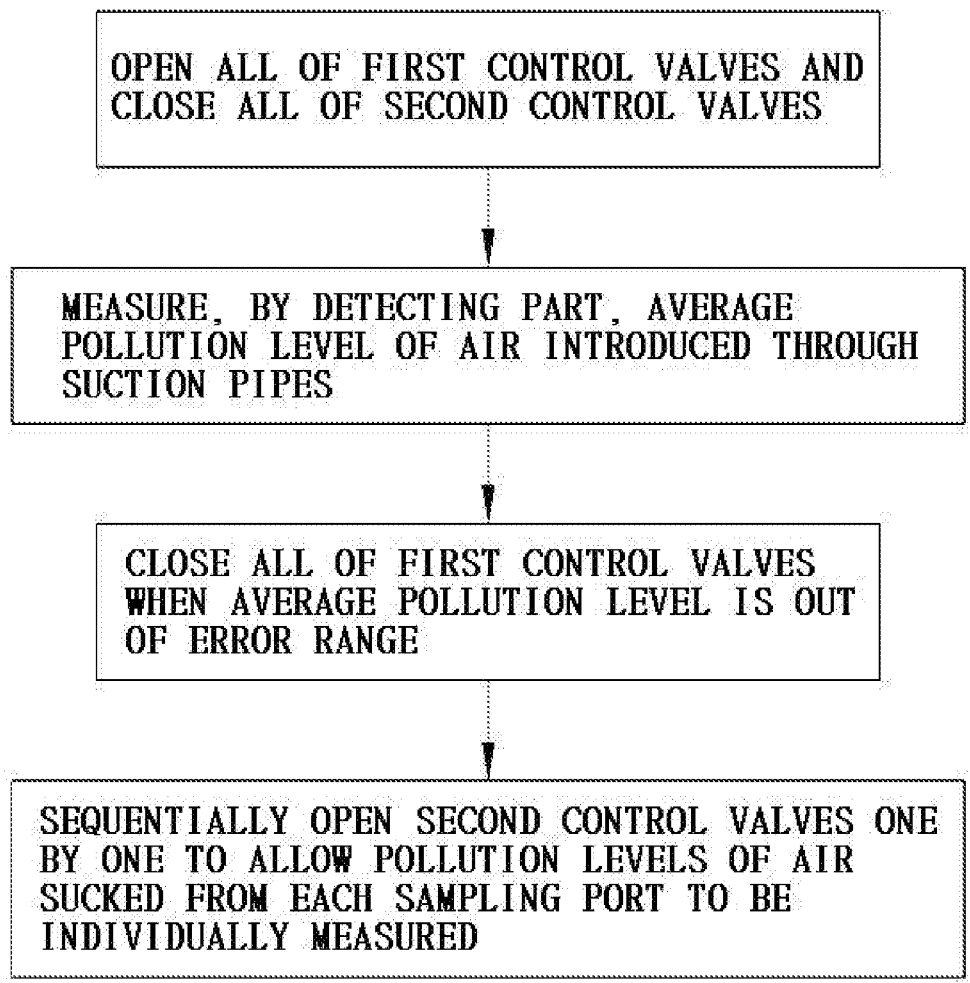
FIG. 5 is a flow chart showing a first example of a multi sampling port monitoring method according to the present invention.

The first example of the monitoring method using the multi sampling port monitoring apparatus 1 according to the present invention shown in FIG. 4 will be described with reference to FIG. 5. First, from the left for convenience of explanation, the branch pipes 300 will be called a first branch pipe 310, a second branch pipe 320, a third branch pipe 330, and a fourth branch pipe 340, and the suction pipes 200 will be called a first suction pipe 210, a second suction pipe 220, a third suction pipe 230, and a fourth suction pipe 240.

In the case in which the event does not occur, in the multi sampling port monitoring apparatus 1 according to the present invention, the first control valves 410 on the first to fourth suction pipes 210, 220, 230, and 240 are opened, and the second control valves 420 on the first to fourth branch pipes 310, 320, 330, and 340 are closed.

When the vacuum pump 830 and the pump in the detecting part 600 are operated, sampling air arrives at the mixing part 500 along the first to fourth suction pipes 210, 220, 230, and 240 through the sampling ports 100, and some of the air arriving at and mixed in the mixing part 500 is introduced into the detecting part 600, such that a pollution level thereof is measured, and the other thereof is discharged through the discharge pipe 831.

Here, air of about 5 lpm is sucked through each of the first to fourth suction pipes 210, 220, 230, and 240, and only 2 lpm of 20 lpm, which is the sum of the sucked flow rate, is introduced into the detecting part 600 and is used to measure the average pollution level and remaining 18 lpm is discharged through the discharge pipe 831.

When the average pollution level measured as described above is out of a predetermined range, all of the first control valves 410 are closed, and only the second control valve 420 on the first branch pipe 310 is opened.

Air of 20 lpm is sucked through the first branch pipe 310, only air of 21 lpm is introduced into the detecting part 600 and is used to measure the pollution level, and remaining 18 lpm is discharged through the discharge pipe 831.

Then, the second control valves 420 on the second branch pipe 320, the third branch pipe 330, and the fourth branch pipe 340 are sequentially opened, such that pollution levels of the sucked air are individually measured, thereby analyzing through which sampling port 100 the pollution source has been introduced.

In addition, in the monitoring method using the multi sampling port monitoring apparatus 1 according to the present invention, the first control valves 410 on the first to fourth suction pipes 210, 220, 230, and 240 are opened and the second control valves 420 on the first to fourth branch pipes 310, 320, 330, and 340 are closed at a predetermined point in time even though the event does not occur during a period in which the pollution levels of the air sucked through the first to fourth branch pipes 310, 320, 330, and 340 are individually measured, thereby making it possible to measure the average pollution level.

That is, the present invention may variously select and use a mode of collectively measuring the average pollution level for each sampling port 100 and a mode of individually measuring the pollution levels for each sampling port 100 as needed.

On the other hand, a second example of a monitoring method using the multi sampling port monitoring apparatus 1 includes a) opening all of the first control valves 410 provided on the plurality of suction pipes 200 and closing all of the second control valves 420; b) measuring, by the detecting part 600, an average pollution level of the air introduced through the suction pipes 200; c) closing all of the first control valves 410 in the case in which the measured average pollution level is out of a preset range; d) opening a plurality of second control valves 420 depending on a predetermined sequence to allow pollution levels of the air sucked from the sampling ports 100 to be measured; and e) closing some of the opened second control valves 420 to allow pollution levels of the air sucked from the sampling ports 100 to be measured, in the case in which the measured average pollution level is out of the preset range, and closing the opened second control valves 420 and opening the closed second control valves 420 to allow pollution levels of the air sucked from the sampling ports 100 to be measured, in the case in which the measured average pollution level is within the preset range.

That is, in the monitoring method according to the present invention, in the case in which a specific event does not occur, all of the first control valves 410 are opened to suck the air through the plurality of sampling ports 100, whereby the average pollution level is measured by the detecting part 600.

In addition, in the case in which the specific event (pollution) occurs, all of the first control valves 410 are closed and some of the second control valves 420 are opened, such that the pollution levels of the air sucked through the sampling ports 100 are measured by the detecting part 600.

Figure 6:
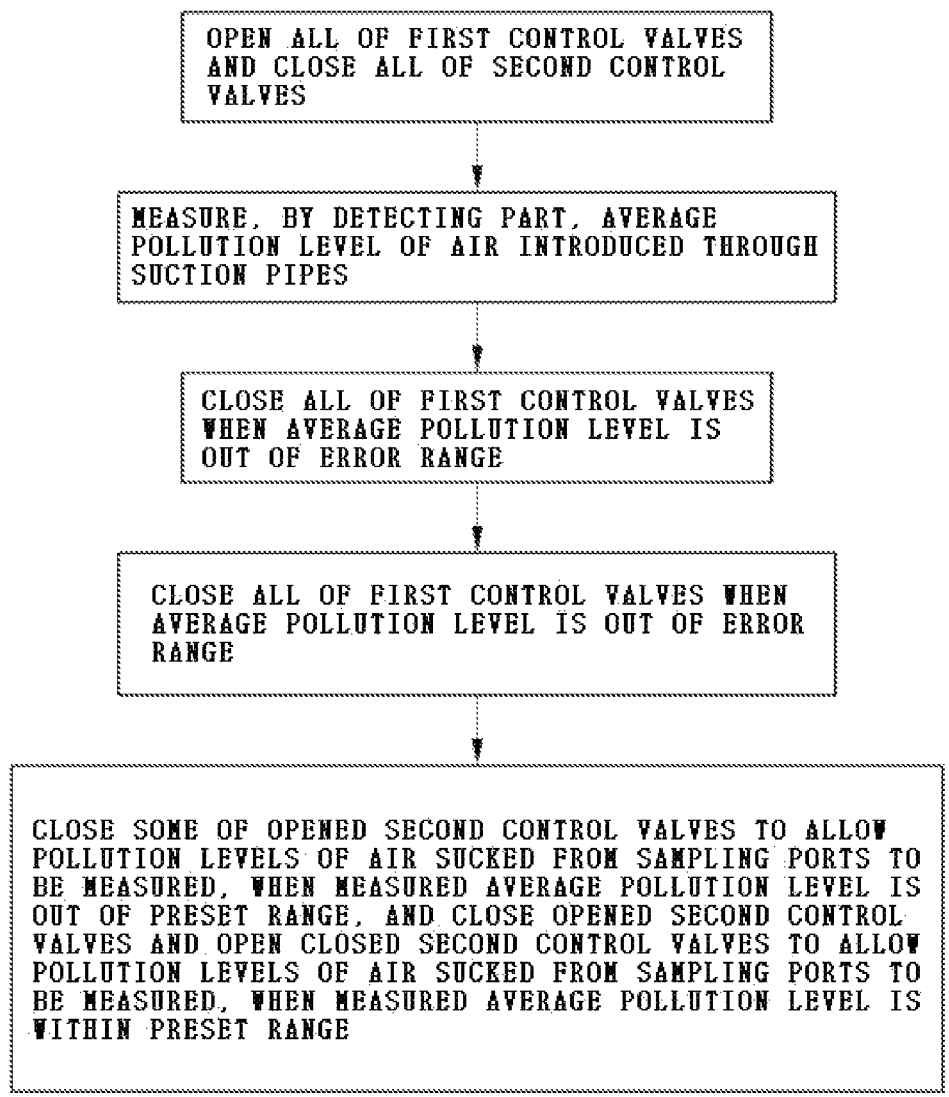
FIG. 6 is a flow chart showing a second example of a multi sampling port monitoring method according to the present invention.

The second example of the monitoring method using the multi sampling port monitoring apparatus 1 according to the present invention will be described with reference to FIG. 6. In the second example, the same monitoring apparatus 1 as the multi sampling port monitoring apparatus used in the first example is used, and in the case in which the event does not occur, in the multi sampling port monitoring apparatus 1 according to the present invention, the first control valves 410 on the first to fourth suction pipes 210, 220, 230, and 240 are opened, and the second control valves 420 on the first to fourth branch pipes 310, 320, 330, and 340 are closed.

When the vacuum pump 830 and the pump in the detecting part 600 are operated, sampling air arrives at the mixing part 500 along the first to fourth suction pipes 210, 220, 230, and 240 through the sampling ports 100, and some of the air arriving at and mixed in the mixing part 500 is introduced into the detecting part 600, such that a pollution level thereof is measured, and the other thereof is discharged through the discharge pipe 831.

Here, air of about 5 lpm is sucked through each of the first to fourth suction pipes 210, 220, 230, and 240, and only 2 lpm of 20 lpm, which is the sum of the sucked flow rate, is introduced into the detecting part 600 and is used to measure the average pollution level and remaining 18 lpm is discharged through the discharge pipe 831.

When the average pollution level measured as described above is out of a predetermined range, all of the first control valves 410 are closed. A process up to now is the same as that of the first example.

Then, all of the second control valves 420 are not opened, but only some of the second control valves 420 are opened. For example, the second control valves 420 on the first and second branch pipes 310 and 320 among the second control valves 420 on the first to fourth branch pipes 310, 320, 330, and 340 are opened, and the second control valves 420 on the third and fourth branch pipes 330 and 340 are closed. In this case, the air is sucked through the first and second branch pipes 310 and 320, such that a pollution level is measured by the detecting part 600.

When the average pollution level measured by the detecting part 600 is out of a predetermined range, the second control valve 420 on the second branch pipe 320 of the opened second control valves 420 on the first and second branch pipes 310 and 320 is closed, and the second control valve 420 of the first branch pipe 310 is maintained in a state in which it is opened. The air is sucked through the first branch pipe 310, such that a pollution level is measured by the detecting part 600. Here, when the average pollution level measured by the detecting part 600 is within the predetermined range, the second control valve 420 on the first branch pipe 310 is closed and the second control valve 420 on the second branch pipe 320 is opened, such that a pollution level of the sucked air is measured.

On the other hand, when the average pollution level measured by the detecting part 600 is within the predetermined range in a state in which the second control valves 420 on the first and second branch pipes 310 and 320 are opened, both of the opened second control valves 420 on the first and second branch pipes 310 and 320 are closed, and the second control valves 420 on the third and fourth branch pipes 330 and 340 are opened. Then, the second control valve 420 on the fourth branch pipe 340 of the opened second control valves 420 on the third and fourth branch pipes 330 and 340 is closed, and the second control valve 420 on the third branch pipe 330 is maintained in a state in which it is opened. The air is sucked through the third branch pipe 330, such that a pollution level is measured by the detecting part 600. Here, when the average pollution level measured by the detecting part 600 is within the predetermined range, the second control valve 420 on the third branch pipe 330 is closed and the second control valve 420 on the fourth branch pipe 340 is opened, such that a pollution level of the sucked air is measured.

The second example of the monitoring method may have an advantage that a pollution point within a space to be measured is rapidly found when the number of branch pipes is plural.

Therefore, the multi sampling port monitoring apparatus 1 and the monitoring method using the same according to the present invention include the plurality of sampling ports 100 so that the air is sucked at several points in the space to be measured, measure the average pollution level of the air sucked from the plurality of sampling ports 100, and allow pollution levels of the air sucked from the sampling ports 100 to be individually or partially measured in the case in which the average pollution level is out of the predetermined range, thereby making it possible to effectively monitor the pollution level in a wide space.

In addition, in the present invention, several sampling ports 100 are disposed in a wide space, and the average pollution level in the space to be measured is managed, thereby making it possible to rapidly find the pollution source at the time of occurrence of the event.

That is, in the present invention, average data on the pollution levels in a zone in which the sampling ports 100 are mounted is managed, thereby making it possible to manage the pollution level in the wide space using one apparatus, and concentrations in each sampling port are sequentially scanned or are individually scanned by a specific sequence in order to recognize the pollution source when the average pollution level rises, thereby making it possible to rapidly find a pollution zone.

Therefore, in present invention, rapid space pollution level mapping and event capture are possible, one measuring instrument (detecting part 600) is used, thereby making it possible to remove an error between measuring instruments, and a cost may be significantly decreased as compared with an existing scheme of using several measuring instruments.

The present invention is not limited to the above-mentioned exemplary embodiments but may be variously applied, and may be variously modified by those skilled in the art to which the present invention pertains without departing from the gist of the present invention claimed in the claims.

DETAILED DESCRIPTION OF MAIN ELEMENTS

1: Multi sampling port monitoring apparatus
100: Sampling port
200: Suction pipe
210, 220, 230, 240: First to fourth suction pipes
300: Branch pipe
310, 320, 330, 340: First to fourth branch pipes
410: First control valve
420: Second control valve
500: Mixing part
600: Detecting part
810: First flow rate adjusting part
820: Second flow rate adjusting part
830: Vacuum pump
831: Discharge pipe

The invention claimed is:

1. A multi sampling port monitoring apparatus for measuring a pollution level in a space to be measured, comprising:
a plurality of sampling ports provided so that air is sucked at several points in the space to be measured;
suction pipes connected to each sampling port;
branch pipes branched from the suction pipes;

a mixing part connected to end portions of the suction pipes and the branch pipes to collect and mix the sucked air;

a detecting part measuring a pollution level of the air passing through the mixing part and then introduced thereinto;

first control valves connected to the suction pipes;

second control valves connected to the branch pipes; and a controlling part controlling the first control valves, the second control valves, and the detecting part, wherein the controlling part performs a control to open the first control valves, thereby allowing an average pollution level of the air sucked from the plurality of sampling ports to be measured or to close the first control valves and open at least one of the plurality of second control valves so that the air flows toward the branch pipes, thereby allowing pollution levels of the air sucked from the sampling ports to be measured.

2. The multi sampling port monitoring apparatus of claim 1, wherein in the case in which the average pollution level of the air sucked from the plurality of sampling ports is out of a predetermined range, the first control valves are closed and the plurality of second control valves are sequentially opened one by one or some of the plurality of second control valves are opened to allow pollution levels of the air sucked from the sampling ports to be measured.

3. The multi sampling port monitoring apparatus of claim 1, wherein the plurality of sampling ports are mounted in one separated space or are each mounted in a plurality of separated spaces.

4. The multi sampling port monitoring apparatus of claim 1, wherein the first control valve is a solenoid valve provided at a front end of the mixing part to collectively control the plurality of suction pipes.

5. The multi sampling port monitoring apparatus of claim 1, wherein the second control valve is a 3-way valve provided at a point of the suction pipe from which the branch pipe is branched.

6. The multi sampling port monitoring apparatus of claim 1, further comprising first flow rate adjusting parts provided on the suction pipes and adjusting a flow rate of the sucked air.

7. The multi sampling port monitoring apparatus of claim 1, further comprising a vacuum pump connected to the mixing part and applying negative pressure so that the air from the sampling ports is sucked.

8. The multi sampling port monitoring apparatus of claim 1, further comprising a second flow rate adjusting part disposed between the mixing part and a vacuum pump.

9. The multi sampling port monitoring apparatus of claim 1, wherein the mixing part has a pipe shape in which pipes each connected to end portions of the plurality of suction pipes and branch pipes are merged as one pipe or has a mixing chamber form including a separate mixing means.

10. A multi sampling port monitoring method using the multi sampling port monitoring apparatus of claim 1, comprising:
   a) opening all of the first control valves provided on the plurality of suction pipes and closing all of the second control valves;
   b) measuring, by the detecting part, an average pollution level of the air introduced through the suction pipes;
   c) closing all of the first control valves in the case in which the measured average pollution level is out of a preset range; and
   d) sequentially opening the second control valves one by one to allow pollution levels of the air sucked from each sampling port to be individually measured.

11. A multi sampling port monitoring method using the multi sampling port monitoring apparatus of claim 1, comprising:
   a) opening all of the first control valves provided on the plurality of suction pipes and closing all of the second control valves;
   b) measuring, by the detecting part, an average pollution level of the air introduced through the suction pipes;
   c) closing all of the first control valves in the case in which the measured average pollution level is out of a preset range;
   d) opening a plurality of second control valves depending on a predetermined sequence to allow pollution levels of the air sucked from the sampling ports to be measured; and
   e) closing some of the opened second control valves to allow pollution levels of the air sucked from the sampling ports to be measured, in the case in which the measured average pollution level is out of the preset range, and closing the opened second control valves and opening the closed second control valves to allow pollution levels of the air sucked from the sampling ports to be measured, in the case in which the measured average pollution level is within the preset range.

* * * * *